United States Patent
De Cicco

(10) Patent No.: US 11,771,869 B2
(45) Date of Patent: Oct. 3, 2023

(54) ELECTROMAGNETIC CONTROL FOR INTRALUMINAL SENSING DEVICES AND ASSOCIATED DEVICES, SYSTEMS, AND METHODS

(71) Applicant: VOLCANO CORPORATION, San Diego, CA (US)

(72) Inventor: Dino De Cicco, Carlsbad, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 884 days.

(21) Appl. No.: 16/351,052

(22) Filed: Mar. 12, 2019

(65) Prior Publication Data

US 2019/0282783 A1     Sep. 19, 2019

Related U.S. Application Data

(60) Provisional application No. 62/642,963, filed on Mar. 14, 2018.

(51) Int. Cl.
| | |
|---|---|
| A61B 8/00 | (2006.01) |
| A61M 25/01 | (2006.01) |
| A61B 8/12 | (2006.01) |
| A61B 8/08 | (2006.01) |
| A61B 1/00 | (2006.01) |
| A61B 90/00 | (2016.01) |

(52) U.S. Cl.
CPC ..... *A61M 25/0127* (2013.01); *A61B 1/00158* (2013.01); *A61B 8/0891* (2013.01); *A61B 8/12* (2013.01); *A61B 8/42* (2013.01); *A61B 8/445* (2013.01); *A61B 8/4263* (2013.01); *A61B 2090/3762* (2016.02); *A61M 2025/0166* (2013.01); *A61M 2205/50* (2013.01)

(58) Field of Classification Search
CPC ...... A61M 25/0127; A61M 2025/0166; A61M 2205/50; A61B 1/00158; A61B 8/0891; A61B 8/12; A61B 8/42; A61B 8/445; A61B 8/4263; A61B 2090/3762; A61B 5/062

See application file for complete search history.

(56) References Cited

U.S. PATENT DOCUMENTS

| | | | |
|---|---|---|---|
| 5,681,260 A | | 10/1997 | Ueda |
| 5,681,860 A | * | 10/1997 | Fisher .................. C07C 233/43 560/174 |

(Continued)

FOREIGN PATENT DOCUMENTS

| | | |
|---|---|---|
| JP | H03109022 A | 5/1991 |
| JP | H0422325 A | 1/1992 |
| JP | 2003260026 A | 9/2003 |

OTHER PUBLICATIONS

International Search Report and Written Opinion dated May 10, 2019 from International Application No. PCT/EP2019/056416 filed Mar. 14, 2019.

*Primary Examiner* — Joel Lamprecht

(57) ABSTRACT

Systems, devices, and methods for using an intraluminal sensing device are provided. The intraluminal sensing device may include a ferrous element disposed at a distal portion of an elongate flexible member configured to be placed in a body lumen of a patient. An external electromagnetic field device may be used to produce an electromagnetic field that may be used to direct the movement of the flexible elongate member within the body lumen.

20 Claims, 6 Drawing Sheets

(56) References Cited

U.S. PATENT DOCUMENTS

| | | |
|---|---|---|
| 7,846,101 B2 | 12/2010 | Eberle et al. |
| 2004/0006268 A1* | 1/2004 | Gilboa ............... A61B 5/06 |
| | | 600/424 |
| 2005/0159798 A1 | 7/2005 | Graumann |
| 2005/0256398 A1 | 11/2005 | Hastings |
| 2007/0021744 A1 | 1/2007 | Creighton |
| 2009/0105579 A1 | 4/2009 | Garibaldi |

* cited by examiner

ELECTROMAGNETIC CONTROL FOR INTRALUMINAL SENSING DEVICES AND ASSOCIATED DEVICES, SYSTEMS, AND METHODS

TECHNICAL FIELD

The present disclosure relates generally to obtaining intraluminal data associated with a body lumen of a patient, and, in particular, to the structure and methods of controlling an intraluminal sensing device. For example, the intraluminal sensing device can include a ferrous tip at a distal portion thereof and may be guided and driven by an electromagnetic field.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy and receive ultrasound echoes reflected from the vessel. The ultrasound echoes are processed to create an image of the vessel of interest.

Operators are typically required to use a guide wire extending through the IVUS device to navigate through the vessels of the patient to an area of interest, such as a lesion. The guide wire is typically directed by hand by the operator. Depending on the location within the body, the size of the IVUS device, and the nature of the operation, a high degree of skill may be required to safety navigate the device. Furthermore, imaging procedures may require real-time fluoroscopy to track to the position of the device. Since an operator is generally required to be within close proximity to the patient to navigate the IVUS device, the operator may be exposed to harmful radiation from fluoroscopy devices during the length of a procedure.

SUMMARY

Systems, devices, and methods for obtaining intraluminal sensing data are provided. A sensing system may include a flexible elongate member configured to be placed in a body lumen of a patient, such as a blood vessel. The flexible elongate member may include an attached ferrous element. The sensing system may also include a device for producing an electromagnetic field. The electromagnetic field may be used to control the position of the flexible elongate member within the body lumen and navigate to a desired location for collecting imaging data. Aspects of the present disclosure provide an intraluminal sensing system that advantageously overcomes the limitations of existing manually navigated devices.

Embodiments of the present disclosure provide an intraluminal sensing system that may include an intraluminal sensing device, including: a flexible elongate member sized and shaped for insertion into a body lumen of a patient, the flexible elongate member comprising a proximal portion and a distal portion; a sensing element disposed at the distal portion of the flexible elongate member and configured to obtain intraluminal data associated with the body lumen; and a ferrous element disposed at the distal portion of the flexible elongate member; an electromagnetic (EM) field device configured to produce an EM field; and a control device configured to direct movement of the flexible elongate member within the body lumen by controlling a direction of the EM field with respect to the ferrous element.

In some embodiments, the sensing element includes an imaging element configured to obtain intraluminal imaging data associated with the body lumen. The imaging element may include an intravascular ultrasound (IVUS) transducer. The control device may be configured to direct the movement of the flexible elongate member within the body lumen along a roadmap based on angiogram data. The control device may be configured to direct the movement of the flexible elongate member within the body lumen along a roadmap based on computed tomography (CT) data.

In some embodiments, the control device comprises a processor configured to automatically direct the flexible elongate member to a target position within the body lumen. The target position may include an aneurysm. The controller may be configured to track a position of the flexible elongate member within the body lumen based on fluoroscopic data. The EM field device may be positioned externally from the patient.

The present disclosure also provides a method of obtaining intraluminal sensing data, which may include: selecting, with a control device, a target position for an intraluminal sensing device within a body lumen of a patient, the intraluminal sensing device comprising a flexible, elongate member sized and shaped for insertion into the body lumen, a sensing element configured to obtain intraluminal sensing data, and a ferrous element; activating an electromagnetic (EM) field device configured to produce an EM field, the EM field device connected to a controller; and controlling, with the controller, the EM field to interact with the ferrous element to move the intraluminal sensing device to the target position.

In some embodiments, the method further includes producing, with the control device, a roadmap using imaging data; and moving the intraluminal sensing device along the roadmap to the target position. The method may also include tracking, with the controller, a position of the flexible, elongate member within the body lumen using data from a fluoroscopy device. The method may include imaging, with an imaging component, a portion of the body lumen at the target position. The imaging component may include an intravascular ultrasound (IVUS) transducer.

In some embodiments, the method further includes moving the intraluminal sensing device to the target position along a roadmap based on intravascular imaging data received by the IVUS transducer. The method may include producing the roadmap with angiogram data co-registered with IVUS data. The method may include producing the roadmap with computed tomography (CT) data co-registered with IVUS data. The step of controlling the EM field may be carried out automatically by a processor.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
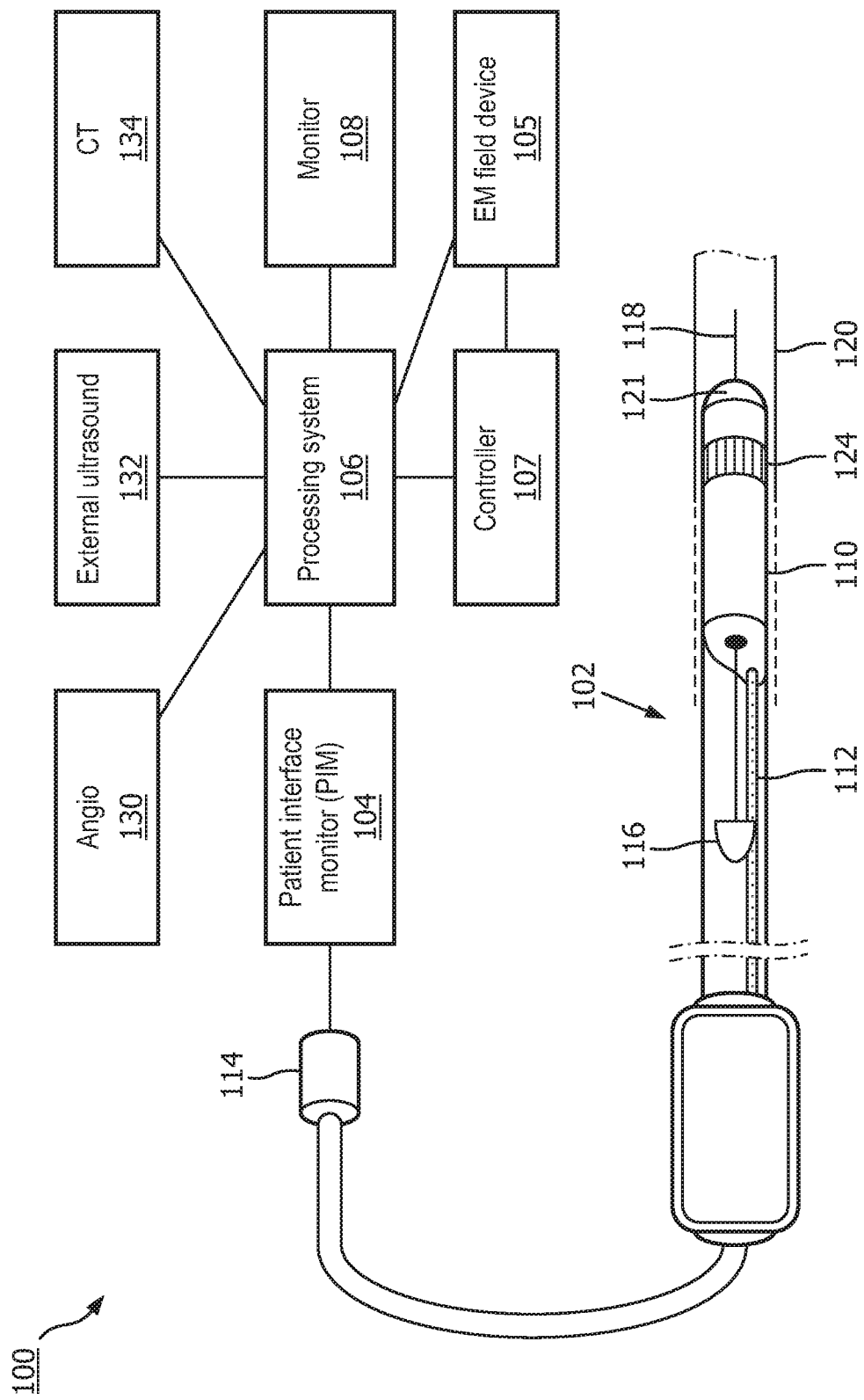
FIG. 1 is a diagrammatic schematic view of an intraluminal sensing system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal sensing system 100, according to aspects of the present disclosure. The intraluminal sensing system 100 can be an intravascular ultrasound (IVUS) imaging system in some embodiments. The intraluminal sensing system 100 may include an intravascular device 102, a patient interface module (PIM) 104, an electromagnetic (EM) field device 105, a console or processing system 106, a controller 107, a monitor 108, an angiography system 130, an external ultrasound system 132, and/or a computed tomography (CT) system 134. The intravascular device 102 is sized and shaped, and/or otherwise structurally arranged to be positioned within a body lumen of a patient. For example, the intravascular device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit one or both of the angiography system 130 and the CT system 134.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical sensing procedures such as angiography, fluoroscopy, CT, IVUS, virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, fluoroscopy, and other medical sensing modalities, or combinations thereof. In some embodiments, the EM field device 105 may be controlled from a remote location such as the control room, such than an operator is not required to be in close proximity to the patient. This may help to prevent operators from being exposed to radiation during medical procedures.

The intravascular device 102, PIM 104, monitor 108, controller 107, EM field device 105, angiography system 130, external ultrasound system 132, and CT system 134 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, the intravascular device 102 emits ultrasonic energy from a transducer array 124 included in scanner assembly 110 mounted near a distal end of the intravascular device 102. The ultrasonic energy is reflected by tissue structures in the medium (such as a vessel 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intravascular device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducers between 1 transducer and 1000 transducers, including values such as 2 transducers, 4 transducers, 36 transducers, 64 transducers, 128 transducers, 500 transducers, 812 transducers, and/or other values both larger and smaller.

The PIM 104 transfers the received echo signals to the processing system 106 where the ultrasound image (including the flow information) is reconstructed and displayed on the monitor 108. The processing system 106 can include a processor and a memory. The console or processing system 106 can be operable to facilitate the features of the intraluminal sensing system 100 described herein. For example, the processor can execute computer readable instructions stored on the non-transitory tangible computer readable medium.

The PIM 104 facilitates communication of signals between the processing system 106 and the scanner assembly 110 included in the intravascular device 102. This communication may include providing commands to integrated circuit controller chip(s) within the intravascular device 102, select particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intravascular device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel 120, such as a cross-sectional IVUS image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

While system 100 and/or device 102 have been described in the context of phased array IVUS imaging, it is understood that the system 100 and/or device 102 can be configured to obtain any suitable intraluminal sensing data. In various embodiments, the device 102 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities. In some embodiments, the device 102 can include an imaging component of any suitable imaging modality, such as optical imaging, optical coherence tomography (OCT), etc. In some embodiments, the device 102 can include any suitable sensing component, including a pressure sensor, a flow sensor, a temperature sensor, an optical fiber, a reflector, a mirror, a prism, an ablation element, a radio frequency (RF) electrode, a conductor, and/or combinations thereof. Generally, the device 102 can include a sensing element to obtain intraluminal data associated with the vessel 120.

In some embodiments, the PIM 104 facilitates communications between the processing system 106 and one or more of the angiography system 130, the external ultrasound system 132, and/or the CT system 134. In some circumstances, the radiography/angiography/fluoroscopy system 130 and/or the CT system 134 may be used to obtain images of the subject's vasculature which may be used as a roadmap (such as roadmap 304 shown in FIGS. 3A, 3B, 4A, and 4B) by a physician or operator of the intravascular device 102 to advance the intravascular device 102 through the vasculature to a target location. In particular, the processing system 106 may be configured to produce such a roadmap 304 with input from the various imaging systems. The controller 107 may be used to control the EM field device 105 to navigate the intravascular device 102 along the roadmap 304. In some embodiments, the roadmap 304 may be translated into a set of instructions or commands to navigate the intravascular device 102. In some embodiments, the controller 107 controls navigation of the intravascular device 102 automatically, such that an operator may select a starting position and an ending position and the controller 107 automatically directs the navigation of the intravascular device 102 along the roadmap 304 to the ending position without intervening controls from an operator. In other embodiments, the controller 107 is configured to follow a roadmap 304 through complex areas of vasculature while an operator may manually navigate the intravascular device 102 through less complicated regions of vasculature. An operator may also be able to manually override the automatic movements of the EM field device 105, such as to prevent a mistake or to image an area of interest along the route of the roadmap 304, as shown in FIGS. 4A and 4B. The roadmap 304 may include an optimized path along the vascular of a patient as well as measurements of the vessels along the path. For example, the roadmap 304 may be created based on a central line through vessels to keep the intravascular device 102 centered and thereby avoid damage to vessel walls.

While the images produced by the angiography system 130 and/or the CT system 134 may be useful to the physician, the patient and/or operator of the system 100 may be exposed to harmful radiation during the imaging process. In order to limit this exposure to radiation, it may be beneficial to control to navigate the intravascular device 102 with an automated system (such as using the EM field device 105), using external ultrasound in conjunction with IVUS data when navigating the intravascular device 102 to the target location, and/or tracking the progress of an intravascular therapy being performed at the target location. In addition to limiting the patient's and operator's radiation exposure, using external ultrasound in conjunction with IVUS advantageously allows intravascular therapies to be performed without radiation shields and radiation equipment which can lower the cost of performing the procedure resulting in savings for the patient and the treatment facility. Furthermore, substituting ultrasound for radiation may allow intravascular therapies to be performed bedside, thereby reducing the number of times the patient is moved, which can be of particular importance in the event that the patient suffered a trauma.

In some embodiments, the IVUS data and/or the external ultrasound data may be co-registered with the 2D or 3D CT image, which may further improve placement accuracy and decrease procedural time. The placement of the intravascular device 102 may be verified with this multi-imaging system, which may improve outcomes versus standard fluoroscopic guidance. In some embodiments, the intravascular device 102 is tracked to the target location as identified on a CT image and/or angiogram (such as a lesion or aneurysm). In some embodiments, a roadmap produced from co-registered IVUS and CT image data may be correlated to fluoroscopic data to further improve accuracy. For example, the processing system 106 may create an imaging loop based on the roadmap and fluoroscopic data to create and adjust commands of the controller 107 to improve the navigation of the intravascular device 102 through the vessels of the patient.

In some embodiments, the intravascular device 102 includes some features similar to traditional solid-state IVUS catheters, such as the EagleEye® catheter available from Volcano Corporation and those disclosed in U.S. Pat. No. 7,846,101 hereby incorporated by reference in its entirety. For example, the intravascular device 102 my include the scanner assembly 110 near a distal end of the intravascular device 102 and a transmission line bundle 112 extending along the longitudinal body of the intravascular device 102. The cable or transmission line bundle 112 can include a plurality of conductors, including one, two, three, four, five, six, seven, or more conductors.

The transmission line bundle 112 terminates in a PIM connector 114 at a proximal end of the intravascular device 102. The PIM connector 114 electrically couples the transmission line bundle 112 to the PIM 104 and physically couples the intravascular device 102 to the PIM 104. In an embodiment, the intravascular device 102 further includes a guidewire exit port 116. Accordingly, in some instances the intravascular device 102 is a rapid-exchange catheter. The guidewire exit port 116 allows a guidewire 118 to be inserted towards the distal end in order to direct the intravascular device 102 through the vessel 120.

In some embodiments, the intravascular device 102 includes a ferrous tip 121 at a distal end of the intravascular device 102. In some embodiments, the ferrous tip 121 may be moved by an external EM field to navigate the intravascular device 102 through the vessel 120. The ferrous tip 121 may be formed out of any type of material responsive to an electromagnetic (EM) field. In some embodiments, the ferrous tip includes one or more metals including iron. These metals may include steel and alloys including steel, such as medical grade stainless steel. The ferrous tip may be sized for insertion in a vessel and may include a tapered shape to facilitate navigation through a vessel. The ferrous tip 121 may be physically connected to other elements of the intravascular device 102, such as the transducer array 124 and/or the scanner assembly 110. In some embodiments, the ferrous tip 121 replaces the guidewire 118 such that no guidewire 118 is used for navigating the intravascular device 102 through the vessel 120. In other embodiments, the intravascular device 102 includes both the guidewire 118 and the ferrous tip 121.

The intraluminal sensing system 100 may also include an EM field device 105 and a controller 107. The EM field device 105 may be configured to produce an EM field to control the position of the intravascular device 102 within the vessel 120. In some embodiments, the EM field device 105 includes a conductive metallic coil that is powered by one or more power sources. The amount of current passing through the coil may be varied to change the strength of the EM field during a procedure. In some embodiments, the one or more power sources are contained within the EM field device 105 (such as small internal batteries), while in other embodiments, the EM field device 105 is powered through an external conductive connection. In some embodiments, the EM field device 105 is configured to be moved across the body of a patient to guide the intravascular device 102. The controller 107 may be any type of control device for adjusting the EM field of the EM field device 105. The controller 107 may include a processor and a memory device. In some embodiments, the controller 107 is disposed within the EM field device 105. In other embodiments, the controller 107 is a part of the processing system 106.

The EM field device 105 may also include a directional component that is configured to change the orientation of a produced EM field. For example, a coil within the EM field device 105 may be positioned along a rotatable platform. The angle of the platform may be varied as a result of commands sent from the controller 107. The variable directionality of the EM field device 105 may provide for precise control of the intravascular device 102 through various types and sizes of vessels.

The positioning of the EM device 105 may be controlled by the controller 107 automatically by a computer or manually by an operator. In some embodiments, the EM field device 105 is configured to be controlled remotely so that an operator is not required to be positioned near the patient. This may decrease the amount of radiation an operator is exposed to if a fluoroscopy procedure is used during the operation.

Figure 2:
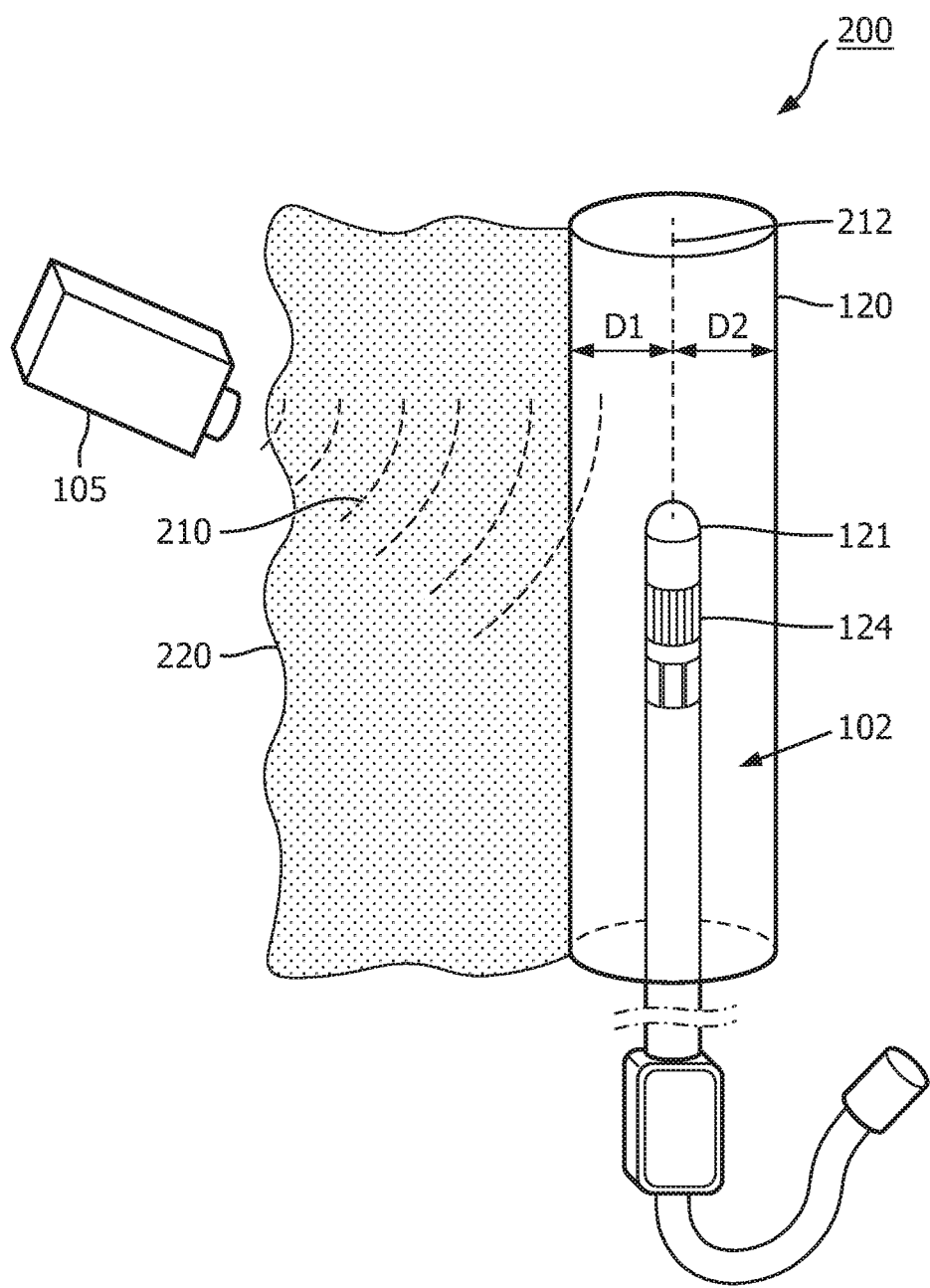
FIG. 2 is an exemplary illustration of an intraluminal device within a vessel and an electromagnetic (EM) field device, according to aspects of the present disclosure.

FIG. 2 is an exemplary illustration 200 of an intravascular device 102 within a body lumen or vessel 120 and an external EM field device 105. In some embodiments, the EM field device 105 may create an EM field 210 which may pass through tissue 220 and walls of the vessel 120 and interact with a ferrous tip 121 within the intravascular device 102. Generally, the ferrous element 121 can be disposed at any position along the length of the intravascular device 102, including the proximal portion, central portion, distal portion, including the distal tip. In some embodiments, the device 102 includes one, two, three, four, or more ferrous elements 121. The interaction of this EM field 210 and the ferrous tip 121 may be used to navigate the intravascular device 102 through the vessel 120. In some embodiments, the EM field device 105 may be configured to control the direction 212 of the intravascular device 102 along the vessel 120 as well as the position of the intravascular device 102 within the vessel. For example, the EM field device 105 may produce an EM field 210 that keeps the intravascular device 102 in the center of the vessel 120 (i.e., such that a distance D1 between the intravascular device 102 to a first portion of the vessel wall is roughly equal to distance D2 between the intravascular device 102 to a second portion of the vessel wall). In other embodiments, the EM field device 105 may be configured to optimize the path of the intravascular device 102 through the vessel 120. For example, the intravascular device 102 may be moved closer to a vessel wall to simplify the path through a complicated section of vasculature or to avoid contact with other tissue or devices within the vessel 120.

In some embodiments, the transducer array 124 of intravascular device 102 may be active during the navigation of the intravascular device 102 through the vessel. The IVUS data received from the transducer array 124 may be used to adjust the position of the intravascular device 102, such as centering the device 102, avoiding obstacles within the vessel, navigating the device 102 from one vessel to another vessel, and/or assisting with other navigational tasks. For example, IVUS data from the transducer array 124 may be processed by the processing system 106 and sent the controller 107 to adjust the EM field 210 so that the intravascular device 102 is centered with respect to the measured boundaries of the vessel 120 as identified by the processed IVUS data.

Figure 3A:
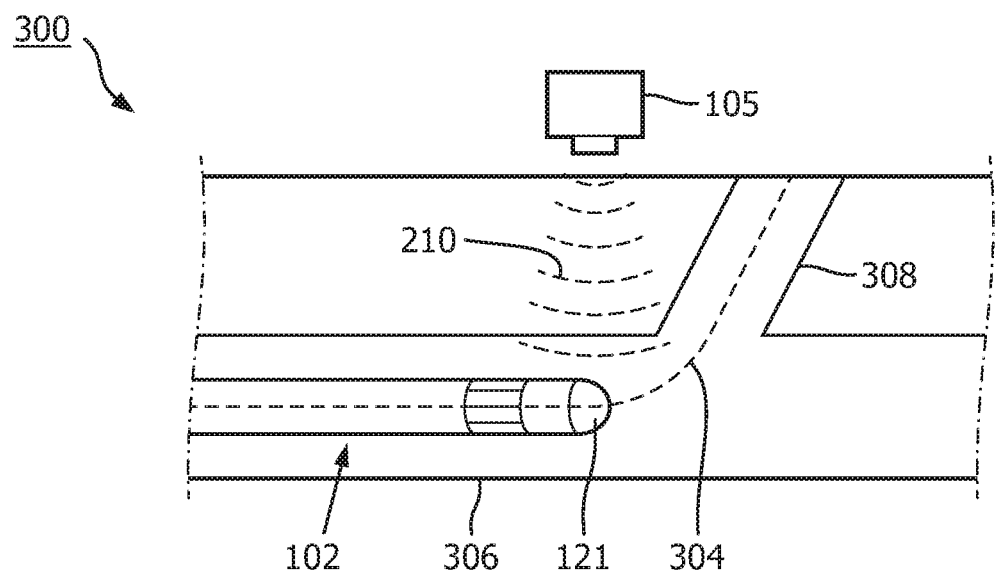
FIG. 3A is an exemplary illustration of an intraluminal device within a first vessel, according to aspects of the present disclosure.
Figure 3B:
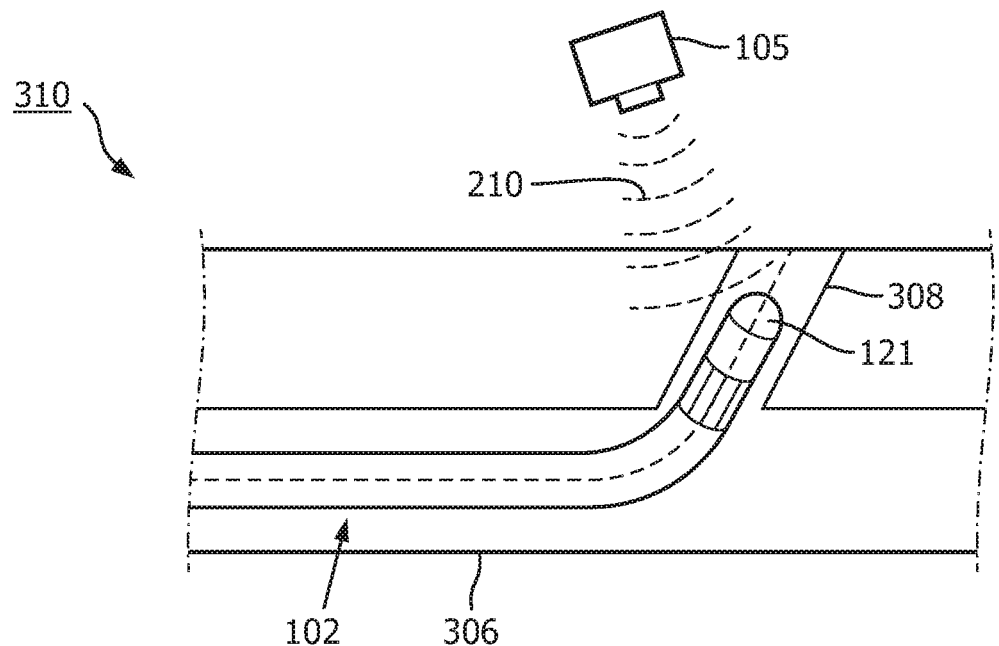
FIG. 3B is an exemplary illustration of an intraluminal device within a second vessel, according to aspects of the present disclosure.
Figure 4A:
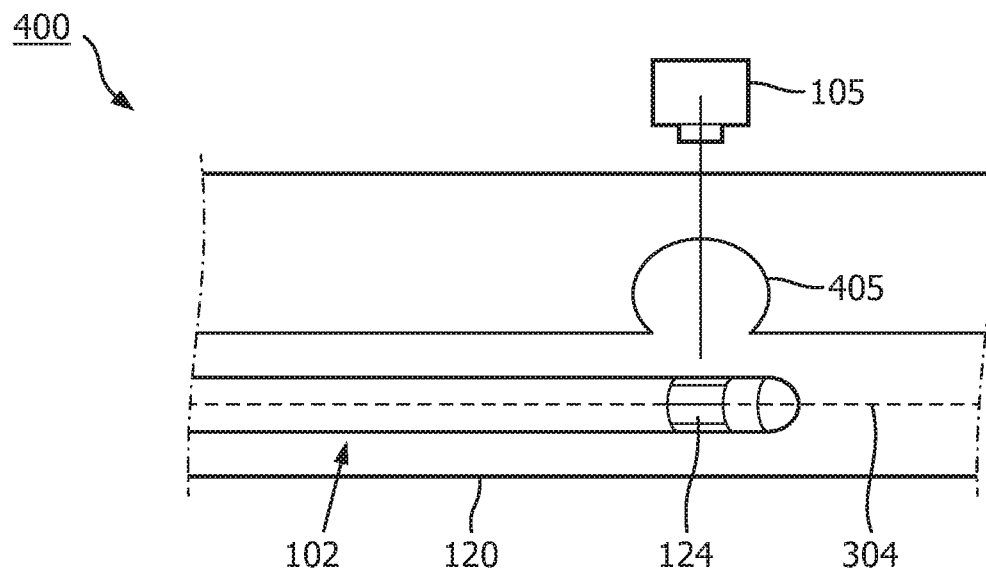
FIG. 4A is an exemplary illustration of an intraluminal device within a vessel, according to aspects of the present disclosure.
Figure 4B:
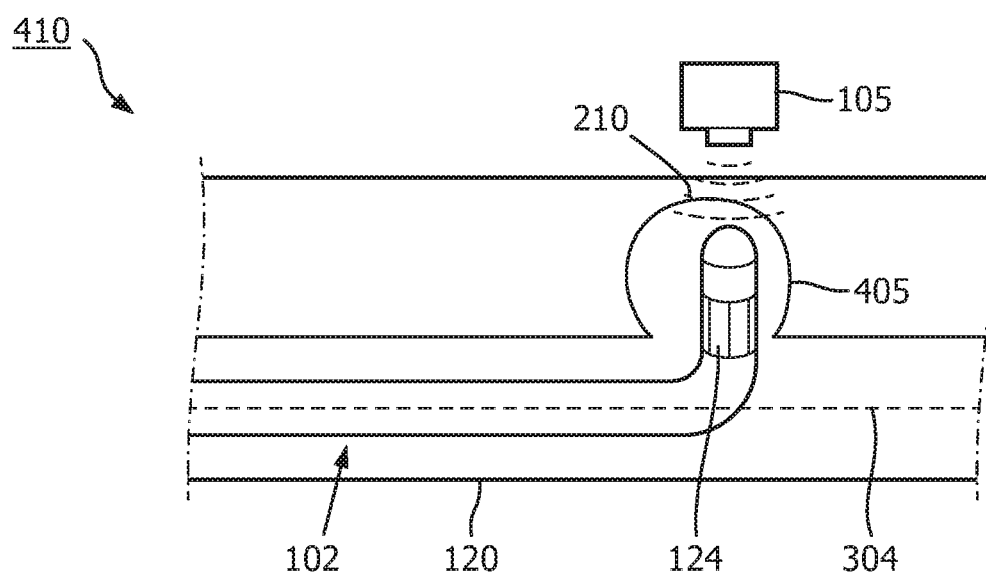
FIG. 4B is another exemplary illustration of an intraluminal device within a vessel, according to aspects of the present disclosure.

FIGS. 3A and 3B are exemplary illustrations 300, 310 showing an intraluminal device 102 that is moved through a vessel 120 through the use of an EM field device 105. In the example of illustration 300, the intravascular device 102 is navigated through a first vessel 306 and a second vessel 308 by the magnetic interaction between the EM field 210 of the EM field device 105 and the ferrous tip 121. The intravascular device 102 may be navigated through the vessels 306, 308 along a roadmap 304. As discussed above, the roadmap 304 may be produced with extraluminal and/or intraluminal imaging data such as radiographic/angiographic/fluoroscopic data, CT data, and IVUS data. The roadmap 304 may represent an optimized route through the vessel of a patient to a desired treatment area, such as a target lesion. In some embodiments, the strength and direction of the EM field 210 may be varied to navigate the device 102 along the roadmap 304. For example, in illustration 310, the roadmap 304 leads through a portion of the first vessel 306 and a portion of the second vessel 308. To navigate the intravascular device 102 along the roadmap 304, the EM field device 105 may be controlled with movements corresponding to the geometry of the vessels 306, 308, externally. As the intravascular device 102 approaches the transition from the first vessel 306 to the second vessel 308, the strength and/or angle of the EM field 210 may be changed to position the intravascular device 102 within the second vessel 308. For example, the strength of the EM field 210 may be increased through input to the controller 107 to pull the ferrous tip toward the EM field device 105 and into the second vessel 308. The angle of the EM field 210 may also be changed to move the intravascular device 102 into a desired position, as shown in the example of FIG. 3B.

FIGS. 4A and 4B are exemplary illustrations 400, 410 showing an intravascular device 102 that is moved through a body lumen or vessel 120 with the use of an EM field device 105. In the example of illustration 400, the intravascular device 102 is navigated along a roadmap 304 that leads through the vessel 120. In some embodiments, the intravascular device 102 is moved along the vessel 120 as a guidewire 118 such as that shown in FIG. 1 is moved along the vessel 306. In this case, the EM field device 105 may not be activated. This method of moving the intravascular device 102 may be used a portion of the vasculature, while the EM field device 105 is activated and used to move the intravascular device 102 for other portions of the vasculature. As discussed above, the intravascular device 102 may include a transducer array 124 which may collect IVUS data as the intravascular device 102 is moved along the vessel 120. The transducer array 124 may collect IVUS data corresponding to a lesion 405 within the vessel 120, and the operator may want to investigate the lesion 405. If this is the case, the EM field device 105 may be activated, producing an EM field 210 that interacts with the ferrous tip 121, as shown in illustration 410. The tip of the intravascular device 102 may be pulled toward the EM field device 105 so that the transducer array 124 is in position to image the lesion 405. After investigating the lesion 405 by collecting IVUS data with the transducer array 124, the EM field device 105 may deactivate the EM field 210 and thereby return the intravascular device 102 to the roadmap 304. In some embodiments, the EM field device 105 may be switched on and off throughout a procedure depending on the roadmap 304 and the use of guidewires 118 or other guidance devices.

Figure 5:
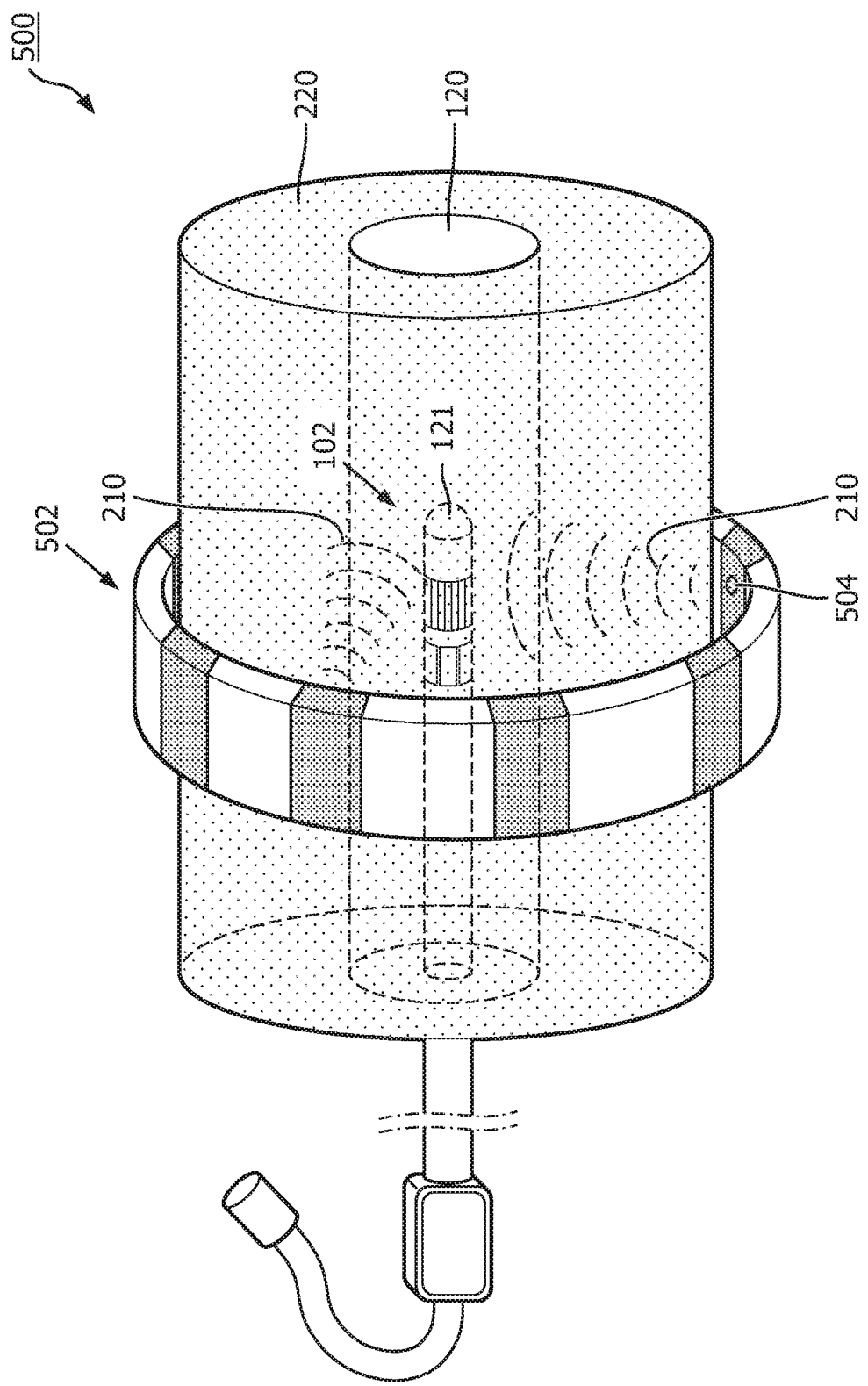
FIG. 5 is an exemplary illustration of an EM field device and intraluminal device, according to aspects of the present disclosure.

FIG. 5 is an exemplary illustration 500 of an exemplary EM field device 502 positioned around the anatomy of a patient, including a vessel 120 and surrounding tissue 220. The EM field device 502 may be similar to the EM field device 105 as shown in FIGS. 1-4 and may be connected to a controller 107 as well as to a power source. In the example of FIG. 5, the EM field device 502 may be positioned around a vessel and surrounding tissue, such as around an extremity of the patient. The EM field device 502 may include one or more EM field production devices 504 that are configured to direct EM fields 210 through the tissue 220 and vessel 120 to guide the intravascular device 102. The EM fields 210 may be directed at various angles and may be produced with various strengths to guide the intravascular device 102 through vessels 120 of various sizes and geometries. The various EM fields 210 may also be used to position the intravascular device in the center of the vessel 120. In some embodiments, the EM field device 502 may be physically moved along the vessel 120 to guide the intravascular device 102.

Figure 6:
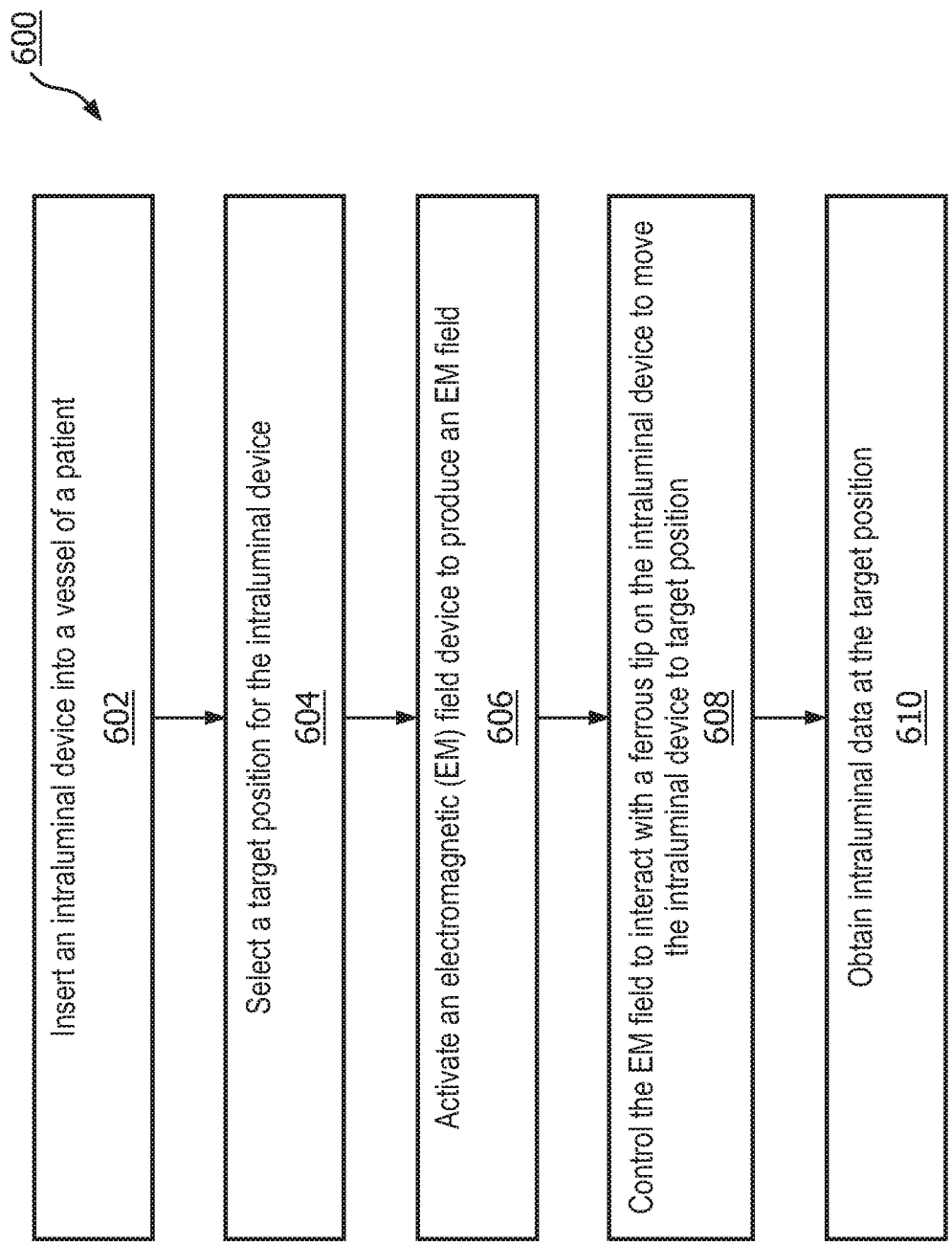
FIG. 6 is a flow diagram of a method of imaging a body lumen, according to aspects of the present disclosure.

FIG. 6 is a flow diagram of a method 600 of imaging a vessel. In some embodiments, the steps of the method 600 may be carried out by the intraluminal sensing system 100 and associated components as shown in FIGS. 1-5. It is understood that the steps of method 600 may be performed in a different order than shown in FIG. 6, additional steps can be provided before, during, and after the steps, and/or some of the steps described can be replaced or eliminated in other embodiments. The steps of the method 600 can be carried out by a manufacturer of the intravascular imaging device.

At step 602, the method 600 may include inserting an intraluminal sensing device into a body lumen of a patient. The step 602 can include, for example, inserting an intravascular device into a vessel of a patient. The intravascular device may be similar to the intravascular device 102 as discussed in reference to FIGS. 1-5. The intravascular device may be sized and shaped to be moved within the vessel and guided to a target location. The intravascular device may include imaging devices such as an IVUS transistor array as well as a ferrous tip. The intravascular device may be connected to a controller or console, such as controller 107 and/or processing system 106 as shown in FIG. 1.

At step 604, the method 600 may include selecting a target position within the anatomy of the patient. The target position may be at a site of a diseased area of a vessel (such as a lesion or aneurysm) or where a previous operation was conducted. The target position may be an area where imaging is desired. The target position may be selected by an operator and may be input into the controller.

At step 606, the method 600 may include activating an EM field device such as EM field device 105 to produce an EM field. The EM field device may be positioned externally and may be moved throughout the procedure to move the intravascular device to the desired position. In some embodiments, the EM field device may be configured to be placed around the anatomy of a patient, such as around an arm or leg, as shown in FIG. 5. In some embodiments, the strength, angle, and position of the EM field produced by the EM field device may be controlled by a controller.

At step 608, the method 600 may include controlling the EM field to interact with the ferrous tip of the intravascular device to move the intravascular device to the target position. In some embodiments, the EM field is used to navigate the intravascular device along a chosen route to the target position. The chosen route may be a roadmap created using imaging data (such as IVUS, angiography, and CT) which may be co-registered for better accuracy. The position and orientation of the intravascular device may be tracked throughout the procedure using fluoroscopy and/or external ultrasound. In some embodiments, the EM field device may be used to navigate the intravascular device automatically, such that an operator inputs a target position and the system automatically produces and follows a roadmap to guide the intravascular device to the target position without requiring further instructions. The EM field device may be turned on and off at various times during an operation as required.

At step 610, the method 600 may include obtaining intraluminal sensing data at the target position with the intraluminal device. For example, the intraluminal sensing data can include imaging data, pressure data, flow data, etc. In some embodiments, the IVUS transducer on the intravascular device is activated at step 610 and sends images of the target position to the processing system.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal sensing system, comprising:
   an intraluminal sensing device, comprising:
      a flexible elongate member sized and shaped for insertion into a body lumen of a patient, the flexible elongate member comprising a proximal portion and a distal portion;
      a sensing element disposed at the distal portion of the flexible elongate member and configured to obtain intraluminal data associated with the body lumen; and
      a ferrous element disposed at the distal portion of the flexible elongate member;
   an electromagnetic (EM) field device positioned externally from the patient and encircling an anatomy of the patient with no intervening structure therebetween between the EM field device and the anatomy of the patient, the EM field device including a plurality of EM field production devices encircling the anatomy of the patient and configured to produce an EM field; and
   a control device configured to direct movement of the flexible elongate member within the body lumen by controlling a direction of the EM field with respect to the ferrous element.

2. The intraluminal sensing system of claim 1, wherein the sensing element comprises an imaging element configured to obtain intraluminal imaging data associated with the body lumen.

3. The intraluminal sensing system of claim 2, wherein the imaging element comprises an intravascular ultrasound (IVUS) transducer.

4. The intraluminal sensing system of claim 1, wherein the control device is configured to direct the movement of the flexible elongate member within the body lumen along a roadmap based on angiogram data.

5. The intraluminal sensing system of claim 1, wherein the control device is configured to direct the movement of the flexible elongate member within the body lumen along a roadmap based on computed tomography (CT) data.

6. The intraluminal sensing system of claim 1, wherein the control device comprises a processor configured to automatically direct the flexible elongate member to a target position within the body lumen.

7. The intraluminal sensing system of claim 1, wherein the controller is configured to track a position of the flexible elongate member within the body lumen based on fluoroscopic data.

8. The intraluminal sensing system of claim 1, wherein the EM field device includes at least six EM field production devices encircling the anatomy of the patient and configured to produce an EM field.

9. A method of obtaining intraluminal sensing data, the method comprising:
   selecting, with a control device, a target position for an intraluminal sensing device within a body lumen of a patient, the intraluminal sensing device comprising a flexible, elongate member sized and shaped for insertion into the body lumen, a sensing element configured to obtain intraluminal sensing data, and a ferrous element;
   activating an electromagnetic (EM) field device positioned externally from the patient and encircling an anatomy of the patient with no intervening structure between the EM field device and the anatomy of the patient, the EM field device configured to produce an EM field, the EM field device connected to a controller, the EM field device comprising a conductive metallic coil powered by one or more power sources to pass current through the conductive metallic coil; and
   controlling, with the controller, the EM field to interact with the ferrous element to move the intraluminal sensing device to the target position.

10. The method of claim 9, further comprising:
    producing, with the control device, a roadmap using imaging data; and moving the intraluminal sensing device along the roadmap to the target position.

11. The method of claim 9, further comprising tracking, with the controller, a position of the flexible, elongate member within the body lumen using data from a fluoroscopy device.

12. The method of claim 9, further comprising imaging, with an imaging component, a portion of the body lumen at the target position.

13. The method of claim 12, wherein the imaging component comprises an intravascular ultrasound (IVUS) transducer.

14. The method of claim 13, further comprising moving the intraluminal sensing device to the target position along a roadmap based on intravascular imaging data received by the IVUS transducer.

15. The method of claim 14, further comprising producing the roadmap with angiogram data co-registered with IVUS data.

16. The method of claim 14, further comprising producing the roadmap with computed tomography (CT) data co-registered with IVUS data.

17. The method of claim 9, wherein the step of controlling the EM field is carried out automatically by a processor.

18. The method of claim 9, wherein the controlling includes controlling a strength of the EM field by controlling an amount of the current passing through the conductive metallic coil.

19. The method of claim 9, wherein the method does not use a guidewire for moving the intraluminal sensing device to the target position.

20. A method of obtaining intraluminal sensing data, the method comprising:
positioning an electromagnetic (EM) field device externally from a patient and encircling an anatomy of the patient with no intervening structure between the EM field device and the anatomy of the patient, the EM field device connected to a controller, the EM field device comprising a conductive metallic coil powered by one or more sources to pass current through the conductive metallic coil;
moving an intraluminal sensing device along a guidewire within a blood vessel of the patient to a target position, the intraluminal sensing device comprising a flexible, elongate member sized and shaped for insertion into the blood vessel, an intravascular ultrasound (IVUS) transducer, and a ferrous element, wherein the EM field device is not activated during the moving;
after the moving, positioning the IVUS transducer to image a lesion within the blood vessel by activating the EM field device positioned externally from the patient to produce an EM field that pulls the ferrous element of the intraluminal sensing device toward the EM field device; and
collecting IVUS data of the lesion using the IVUS transducer positioned by the activation of the EM field device.

* * * * *